United States Patent [19]

Meiser et al.

[11] 4,147,791
[45] Apr. 3, 1979

[54] 1-SUBSTITUTED-1,2,4-TRIAZOLE FUNGICIDAL COMPOSITIONS AND METHODS FOR COMBATTING FUNGI THAT INFECT OR ATTACK PLANTS

[75] Inventors: Werner Meiser; Karl H. Büchel; Wolfgang Krämer, all of Wuppertal; Ferdinand Grewe, Burscheid, all of Fed. Rep. of Germany

[73] Assignee: Bayer Aktiengesellschaft, Leverkusen, Fed. Rep. of Germany

[21] Appl. No.: 550,242

[22] Filed: Feb. 14, 1975

Related U.S. Application Data

[63] Continuation-in-part of Ser. No. 318,963, Dec. 27, 1972, Pat. No. 3,912,752.

[30] Foreign Application Priority Data

Jan. 11, 1972 [DE] Fed. Rep. of Germany ....... 2201063

[51] Int. Cl.² ..................... A01N 9/22; A01N 21/00
[52] U.S. Cl. ................................. 424/269; 260/308 R
[58] Field of Search ..................... 260/308 R; 424/269

[56] References Cited

U.S. PATENT DOCUMENTS

| 3,755,349 | 8/1973 | Timmler et al. | 260/309 |
| 3,890,442 | 6/1975 | Meiser et al. | 424/269 |
| 3,897,438 | 7/1975 | Draber et al. | 260/296 R |
| 3,912,752 | 10/1975 | Meiser et al. | 260/308 R |
| 3,974,174 | 8/1976 | Büchel et al. | 260/308 R |
| 4,002,763 | 1/1977 | Meiser et al. | 424/269 |
| 4,060,623 | 11/1977 | Meiser et al. | 424/269 |

FOREIGN PATENT DOCUMENTS 2201063  8/1972 Fed. Rep. of Germany.

Primary Examiner—Raymond V. Rush
Assistant Examiner—Diana G. Rivers
Attorney, Agent, or Firm—Sprung, Felfe, Horn, Lynch & Kramer

[57] ABSTRACT 1-substituted-1,2,4-triazoles of the formula

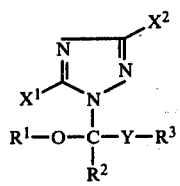

in which
X¹ represents hydrogen or an alkyl radical,
X² represents hydrogen or an alkyl radical,
R¹ represents an alkyl, alkenyl, alkynyl, cycloalkyl, cycloalkenyl or optionally substituted aryl or aralkyl radical,
R² represents hydrogen or an alkyl, alkenyl, alkynyl, cycloalkyl, cycloalkenyl or optionally substituted aryl or aralkyl radical,
R³ represents hydrogen or an alkyl, alkenyl, alkynyl, cycloalkyl, cycloalkenyl or optionally substituted aryl or aralkyl radical, and
Y represents a keto group or a functional keto derivative, which possess fungicidal properties.

3 Claims, No Drawings

1-SUBSTITUTED-1,2,4-TRIAZOLE FUNGICIDAL COMPOSITIONS AND METHODS FOR COMBATTING FUNGI THAT INFECT OR ATTACK PLANTS

This application is a continuation-in-part of application Ser. No. 318,963, filed Dec. 27, 1972, now U.S. Pat. No. 3,912,752.

The present invention relates to and has for its objects the provision of particular new 1-substituted-1,2,4-triazoles, i.e. 1-[1',2',4'-(optionally 2',5'-substituted)-triazolyl-(1')]-1-alkoxy- or -aroxy-butanones and ketals thereof, as well as salts thereof, which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It is known from U.S. Pat. No. 2,425,341 that n-dodecylguanidine actate (Compound A) possesses fungicidal activity, both protective and curative. Since the toleration of this compound by some types of fruit is low, however, it can only be used preceding blossoming.

It is also known from Swiss Patent Specification No. 488,713 that 1-trityl-1,2,4-triazole (Compound B) is fungicidally active. However, its action is not always entirely satisfactory if low amounts and concentrations are used.

The present invention provides compounds which are 1,2,4-triazole derivatives or salts thereof, the 1,2,4-triazole derivatives being of the general formula

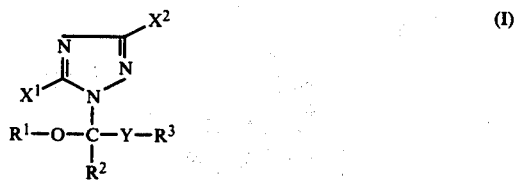

in which
X$^1$ represents hydrogen or an alkyl radical,
X$^2$ represents hydrogen or an alkyl radical,
R$^1$ represents an alkyl, alkenyl, alkynyl, cycloalkyl, cycloalkenyl or optionally substituted aryl or aralkyl radical,
R$^2$ represents hydrogen or an alkyl, alkenyl, alkynyl, cycloalkyl, cyloalkenyl or optionally substituted aryl or aralkyl radical,
R$^3$ represents hydrogen or an alkyl, alkenyl, alkynyl, cycloalkyl, cycloalkenyl or optionally substituted aryl or aralkyl radical, and
Y represents a keto group or a functional keto derivative.

Surprisingly, the compounds according to the invention show a considerably higher fungicidal action than the n-dodecyl-guanidine acetate and 1-trityl-1,2,4-triazole known from the prior art, which are the nearest active compounds of similar mode of action. The substances according to the invention thus represent an enrichment of the art.

In formula I hereinabove X$^1$ and X$^2$ can be the same or different and preferably represent hydrogen or a straight-chain or branched lower alkyl radical with 1 to 3 carbon atoms, especially methyl.

R$^1$ preferably represents a straight-chain or branched alkyl radical with 1 to 8, especially 1 to 4, carbon atoms, a straight-chain or branched alkenyl radical with 2 to 6, especially 3 to 6, carbon atoms, a straight-chain or branched alkynyl radical with 2 to 6, especially 3 to 6, carbon atoms, a cycloalkyl or cycloalkenyl radical with 5 to 7, especially 5 or 6, carbon atoms, an optionally substituted aryl radical with 6 to 10 carbon atoms or an optionally substituted aralkyl radical with 6 to 10 carbon atoms in the aryl moiety and 1 or 2 carbon atoms in the alkyl moiety. Preferred substituents of the two last-mentioned radicals include: halogen, especially fluorine, chlorine or bromine, nitro, amino, straight-chain or branched alkyl with 1 to 6, especially 1 to 4, carbon atoms, alkoxy with 1 to 4, especially 1 or 2, carbon atoms, alkylthio with 1 to 4, especially 1 or 2, carbon atoms, haloalkyl with 1 to 2 carbon atoms and 1 to 5 halogen atoms, especially fluorine or chlorine, haloalkylthio with 1 or 2 carbon atoms and 3 to 5 halogen atoms (for example difluorochloromethyl), haloalkyl sulfonyl with 1 or 2 carbon atoms and 1 halogen atom, especially chlorine (for example chloromethylsulfonyl), or o- or p-linked phenyl.

R$^2$ and R$^3$ preferably represent hydrogen or any of the radicals mentioned for R$^1$, and R$^2$ more preferably represents hydrogen, a straight-chain or branched alkyl radical with 1 to 6, especially 1 to 4, carbon atoms, a straight-chain or branched alkenyl radical with 2 to 6, especially 2 to 4, carbon atoms, a straight chain or branched alkynyl radical with 2 to 6, especially 2 to 4, carbon atoms, a cycloalkyl or cycloalkenyl radical with 5 to 7, especially 5 or 6, carbon atoms, an optionally substituted aryl radical with 6 to 10 carbon atoms or an optionally substituted aralkyl radical with 6 to 10 carbon atoms in the aryl moiety and 1 or 2 carbon atoms in the alkyl moiety (for example phenyl or benzyl). Preferred substituents of the aryl or aralkyl radicals include: halogen, especially fluroine, chlorine or bromine, straight-chain or branched alkyl with 1 to 4 carbon atoms or haloalkyl with 1 or 2 carbon atoms and 2 to 5 halogen atoms, especially fluorine or chlorine.

Y preferably represents a carbonyl group, which can optionally be present in the hydrated form —C(OH)$_2$—, or a ketal group —C(OR)$_2$—, wherein R represents an alkyl radical, preferably with 1 or 2 carbon atoms, or an oxime —C=NOH.

The invention also provides a process for the production of a compound as defined above in which
(a) a haloether-ketone of the general formula

in which
R$^1$, R$^2$, R$^3$ and Y have the abovementioned meanings, and
Hal represents halogen, especially chlorine or bromine
is reacted with a 1,2,4-triazole of the general formula

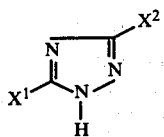 (III)

in which X¹ and X² have the abovementioned meanings, optionally in the presence of an acid-binding agent and optionally in the presence of a diluent, or (b) a hydroxy-ether-ketone of the general formula

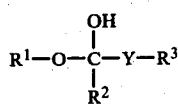 (IV)

in which R¹, R² and R³ have the abovementioned meanings,
is reacted with a 1,2,4-triazole of the formula (III), optionally in the presence of a diluent and optionally in the presence of a dehydrating agent, or (c) a hydroxy-ether-ketone of the formula (IV) is reacted with a compound of the general formula

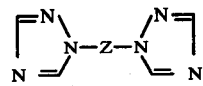 (V)

in which Z represents the SO or CO group, optionally in the presence of a diluent, or (d) a compound of the general formula

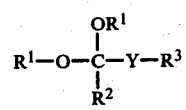 (VI)

in which R¹, R² and R³ have the abovementioned meanings,
is reacted with a 1,2,4-triazole hydrochloride of the general formula

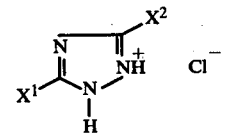 (VII)

in which X¹ and X² have the abovementioned meanings, optionally in the presence of a diluent and optionally in the presence of an acid catalyst.

If the compound is desired in the form of a salt, the process may of course include a step of converting the product of the above reactions into a salt by any convenient method.

If [ω-bromo]-[ω-(2',6'-dichloro)-phenoxy]-acetophenone and 1,2,4-triazole are used as the starting substances in process variant (a), the course of the reaction can be represented by the following equation

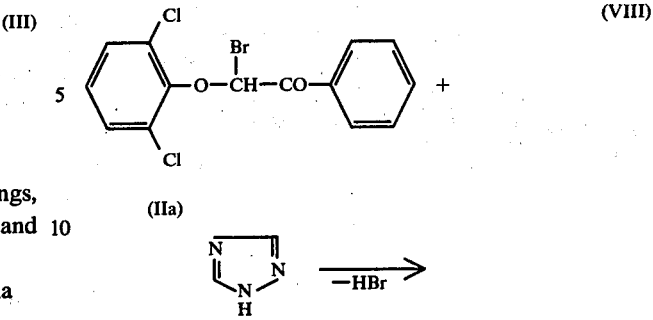 (VIII)

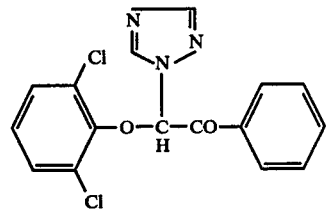 (IIIa)

(40)

If [1-hydroxy]-[1-(2',4'-dichloro)-phenoxy]-3,3-dimethylbutan-2-one and 1,2,4-triazole are used as the starting substances in process variant (b), the course of the reaction can be represented by the following equation:

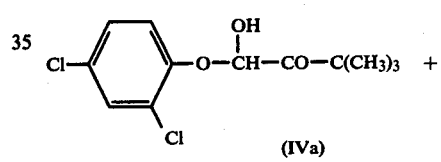

(IVa)

(IIIa)

 (IX)

(1)

If [1-hydroxy]-[1-(2',4'-dichloro)-phenoxy]-3,3-dimethyl-butan-2-one and thionyl-bis-1,2,4-triazole are used as starting substances in process variant (c), the course of the reaction can be represented by the following equation:

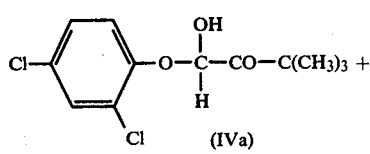

(IVa)

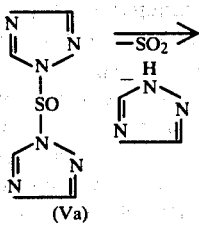

(Va)

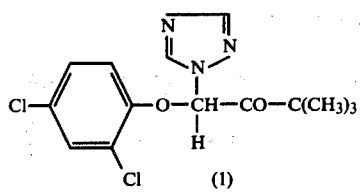

If 1-bis-[(2',4'-dichloro)-phenoxy]-1-phenyl-3,3-dimethyl-butan-2-one and 1,2,4-triazole hydrochloride are used as the starting substances in process variant (d), the course of the reaction can be represented by the following equation:

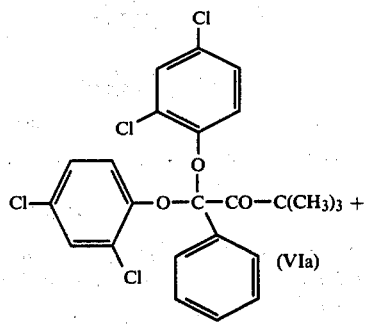

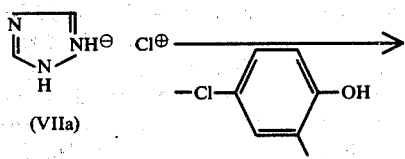

(VIIa)

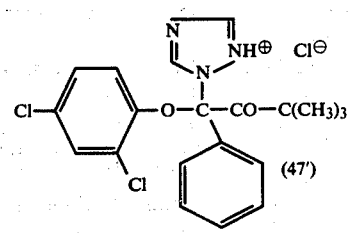

The following may be mentioned as examples of the compounds of the formula (II) which can be used according to the invention: 1-bromo-1-phenoxy-3,3-dimethyl-butan-2-one, 1-bromo-1-(4'-chlorophenoxy)-3,3-dimethyl-butan-2-one, 1-bromo-1-(3'-chlorophenoxy)-3,3-dimethyl-butan-2-one, 1-bromo-1-(2',4'-dichloropheonxy)-3,3-dimethyl-butan-2-one, 1-bromo-1-(2',6'-dichlorophenoxy)-3,3-dimethyl-butan-2-one, 1-bromo-1-(2', 5'-dichlorophenoxy)-3,3-dimethyl-butan-2-one, 1-bromo-1-(4'-methoxyphenoxy)-3,3-dimethyl-butan-2-one, 1-bromo-1-(2'-methylphenoxy)-3,3-dimethyl-butan-2-one, 1-bromo-1-(2',3'-dichloropheonoxy)-3,3-dimethyl-butan-2-one, 1-bromo-1-(4'-bromophenoxy)-3,3-dimethyl-butan-2-one, 1-bromo-1-(4'-fluorophenoxy)-3,3-dimethyl-butan-2-one, 1-bromo-1-(2',4',6'-trichlorophenoxy)-3,3-dimethyl-butan-2-one, 1-bromo-1-(4'-tert.-butyl-phenoxy)-3,3-dimethyl-butan-2-one, 1-bromo-1-(4'-isopropyl-phenoxy)-3,3-dimethyl-butan-2-one, 1-bromo-1-(2'-methyl-4'-chlorophenoxy)-3,3-dimethyl-butan-2-one, 1-bromo-1-(4'-trifluoromethyl-phenoxy)-3,3-dimethyl-butan-2-one, 1-bromo-1-(4'-nitrophenoxy)-3,3-dimethyl-butan-2-one, 1-bromo-1-(2'-nitrophenoxy)-3,3-dimethyl-butan-2-one, 1-bromo-1-(p-diphenoxy)-3,3-dimethyl-butan-2-one, 1-bromo-1-(o-diphenoxy)-3,3-dimethyl-butan-2-one, ω-bromo-ω-phenoxy-actophenone, ω-bromo-ω-(4'-chlorophenoxy)-acetophenone, ω-bromo-ω-(3'-chlorophenoxy)-acetophenone, ω-bromo-ω-(2',4'-dichlorophenoxy)-acetophenone, ω-bromo-ω-(4'-methylphenoxy)-acetophenone, ω-chloro-ω-(2'-chloro-4'-methylphenoxy)-acetophenone, ω-chloro-ω-(2'-methyl-4'-chloro-phenoxy)-acetophenone, ω-bromo-ω-(2'-methyl-phenoxy)-acetophenone, ω-chloro-ω-(2',4'-dichlorophenoxy)-4-chloroacetophenone, and ω-bromo-ω-(2',6'-dichlorophenoxy)-acetophenone.

Many of the halogen compounds of the formula (II) used as starting substances are known, and those which are not yet known can be prepared according to known processes, for example by reacting a compound of the formula $$R^1\text{—OH} \qquad (VIII)$$

in which $R^1$ has the meaning indicated above, with a haloketone of the formula $$\text{Hal-}\underset{\underset{R^2}{|}}{\overset{\overset{H}{|}}{C}}\text{—CO—R}^3 \qquad (IX)$$

in which $R^2$ and $R^3$ have the abovementioned meanings, and

Hal represents halogen, preferably chlorine or bromine.

The active hydrogen atom which still remains may be subsequently replaced by halogen in the usual manner and the keto group is optionally converted into a functional derivative.

The following may be mentioned as examples of the 1,2,4-triazoles of the formula (III) which can be used according to the invention: 1,2,4-triazole, 3-methyl-1,2,4-triazole and 3,5-dimethyl-1,2,4-triazole. These compounds are known.

The following may be mentioned as examples of the compounds of the formula (IV) which can be used according to the invention: ω-hydroxy-ω-methyl-ω-phenoxy-acetophenone, ω-hydroxy-ω-methyl-ω-(4'-chlorophenoxy)-acetophenone, ω-hydroxy-ω-methyl-ω-(2',4'-dichlorophenoxy)-acetophenone, ω-hydroxy-ω-phenoxy-acetophenone, ω-hydroxy-ω-(4'-chlorophenoxy)acetophenone, ω-hydroxy-ω-(2',4'-dichlorophenoxy)-acetophenone, ω-hydroxy-ω-(3'-chlorophenoxy)-acetophenone, ω-hydroxy-ω-(2'-chlorophenoxy)-acetophenone, ω-hydroxy-ω-(2',5'-dichlorophenoxy)-acetophenone, ω-hydroxy-ω-(2',6'-dichlorophenoxy)-acetophenone, ω-hydroxy-ω-(4'-fluorophenoxy)-acetophenone, ω-hydroxy-ω-(4'-bromophenoxy)-acetophenone, ω-hydroxy-ω-(4'-methylphenoxy)-acetophenone, 1-hydroxy-1-phenoxy-3,3-dimethyl-butan-2-one, 1-hydroxy-1-(4'-chlorophenoxy)-3,3-dimethyl-butan-2-one, 1-hydroxy-1-(2',4'- dichlorophenoxy)-3,3-dimethyl-butan-2-one, 1-hydroxy-1-(2',6'-dichlorophenoxy)-3,3-dimethyl-butan-2-one and 1-hydroxy-1-(2',5'-dichlorophenoxy)-3,3-dimethyl-butan-2-one.

The compounds of the formula (IV) can be prepared from the halogen derivatives of the formula (II) in the usual manner or in accordance with known processes, for example by the reaction of α-β-diketones or α-ketoaldehydes with alcohols in accordance with the following equation, with $R^1$, $R^2$ and $R^3$ in the formulae having the meanings indicated above:

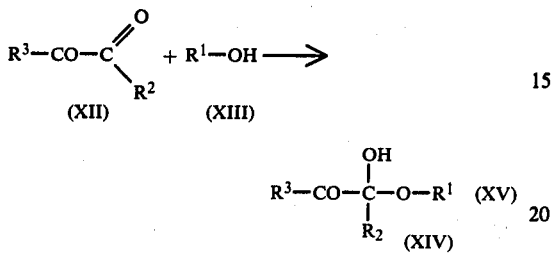

The keto group of the ketones thus produced can optionally be converted into functional derivatives in accordance with customary methods.

The thionyl- or carbonyl-bis-1,2,4-triazoles used as starting substances for process variant (c) have the formula (V); they have hitherto been unknown but can be readily prepared according to known processes, e.g. Angew. Chem. 68, page 754 (1956).

The starting substances for the process variant (d) are generally defined by the formula (VI). In this case $R^3$ can preferably represent hydrogen as well as any of the preferred radicals mentioned above in connection with $R^3$.

The following may be mentioned as examples of the compounds of the formula (VI) which can be used according to the invention: 1-phenyl-1,1-bis-phenoxy-3,3-dimethyl-butan-2-one, 1-phenyl-1,1-bis-(4'-chlorophenoxy)-3,3-dimethyl-butan-2-one, 1-phenyl-1,1-bis-(3'-chlorophenoxy)-3,3-dimethyl-butan-2-one, 1-phenyl-1,1-bis-(2',4'-chlorophenoxy)-3,3-dimethyl-butan-2-one, 1-phenyl-1,1-bis-(4'-methoxyphenoxy)-3,3-dimethyl-butan-2-one, 1-phenyl-1,1-bis-(4'-methylphenoxy)-3,3-dimethyl-butan-2-one, 1-(4-chlorophenyl)-1,1-bis-phenoxy-3,3-dimethyl-butan-2-one, 1-(4-chlorophenyl)-1,1-bis-(4'-chlorophenoxy)-3,3-dimethyl-butan-2-one, 1-(4-chlorophenyl)-1,1-bis-(2',4'-chlorophenoxy)-3,3-dimethyl-butan-2-one, 1-(4-chlorophenyl-1,1-bis-(4'-methylphenoxy)-3,3-dimethyl-butan-2-one, 1-(4-chlorophenyl)-1,1-bis-(4'-nitrophenoxy)-3,3-dimethyl-butan-2-one, ω-phenyl-ω,ω-bis-phenoxy-acetophenone, ω-phenyl-ω,ω-bis-(4'-chlorophenoxy)-acetophenone, ω-methyl-ω,ω-bis-phenoxy-acetophenone, ω-methyl-ω,ω-bis-(4'-chlorophenoxy)-acetophenone, ω-methyl-ω,ω-bis-(2',4'-dichlorophenoxy)-acetophenone, ω-methyl-ω,ω-bis-(2',6'-dichlorophenoxy)-acetophenone, ω-ethyl-ω,ω-bis-(4'-chlorophenoxy)-acetophenone, 2-dimethoxy-butan-3-one, 2-diethoxy-butan-3-one, 2-bis-phenoxy-butan-3-one, 2-dimethoxy-ethan-2-one, α,α-bis-methyl-benzil-ketal, α,α-bis-ethyl-benzil-ketal, 1,1-dimethoxy-1,2-bis-cyclohexyl-ethan-2-one, 1,1-dimethoxy-1,2-bis-cyclopentyl-ethan-2-one, 2,5-dimethyl-3,3-dimethoxy-hexan-4-one, 2,5-dimethyl-3,3-diethoxy-hexan-4-one and 2,5-dimethyl-3,3-bis-phenoxy-hexan-4-one.

Many of the ketals used as starting substances of the formula (VI) are known. Those which are not yet known can be prepared according to customary processes, e.g. J. Chem. Soc. (London) (1970) 3, 462-464, Liebigs Ann. Chem. 735 (1970) 145-157. These ketals can furthermore be prepared by Reformatzky synthesis or Grignard synthesis which leads to an aralkyl-ketone, and also by bromination on the carbon atom adjacent to the keto group and by reaction of the resulting dibromo-ketone with an alcoholate or phenolate, in accordance with the following two equations:

Equation XVI:

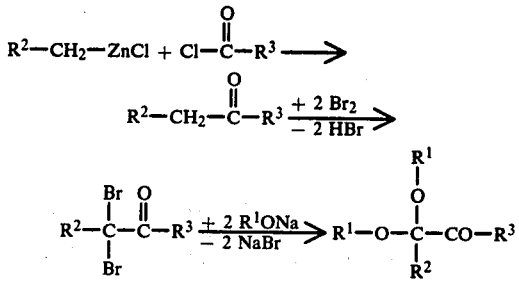

Equation XVII:

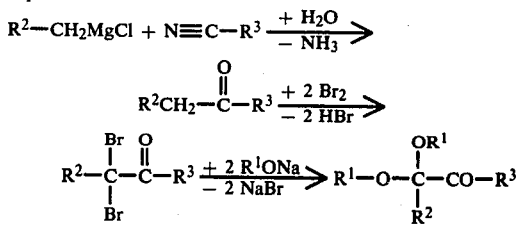

The compounds of formula (VII) may for example be the hydrochlorides of any of the compounds of formula (III) specified herein.

The preferred salts of the 1,2,4-triazole derivatives of the formula (I) are those with physiologically tolerated acids. Examples of such acids are the hydrogen halide acids, for example hydrobromic acid and, especially, hydrochloric acid, phosphoric acid, monofunctional and bifunctional carboxylic acids and hydroxycarboxylic acids, for example acetic acid, maleic acid, succinic acid, fumaric acid, tartaric acid, citric acid, salicyclic acid, sorbic acid, lactic acid, and 1,5-naphthalene-disulfonic acid.

Preferred diluents for process variant (a), involving reaction of the halogen derivatives of the formula (II) with 1,2,4-triazoles of the formula (III), are polar organic solvents. Preferred examples include nitriles, such as acetonitrile; sulfoxides, such as dimethylsulfoxide; formamides, such as dimethylformamide; ketones, such as acetone; ethers, such as diethyl-ether or tetrahydrofuran; nitroalkanes, such as nitromethane; and chlorinated hydrocarbons, such as methylene chloride and chloroform.

The reaction of variant (a) is preferably carried out in the presence of an acid-binding agent. Preferably, an appropriate excess of 1,2,4-triazole is used for this purpose. However, it is also possible to add any of the other organic acid-binding agents usually employed, such as lower tertiary alkylamines or aralkylamines, for example triethylamine or dimethylbenzylamine, it is also possible to add inorganic acid-binding agents, for example potassium carbonate.

In process variant (a) the reaction temperatures can be varied over a wide range. In general the reaction is carrier out at about 20° to 150° C., preferably about 80° C. to 120° C.

In carrying out process variant (a), it is preferred to use about 1 mole of 1,2,4-triazole and about 1 mole of acid-binding agent for each mole of the compound of the formula (II).

To isolate the product of the formula (I), the solvent may be evaporated off in vacuo and the residue may be taken up in an orgaic solvent. This may be followed by extraction with water to remove the 1,2,4-triazolyl hydrochloride which is produced at the same time, and evaporation of the solution to dryness. The base may be isolated from the residue by recrystallization, and the salt by treatment with the appropriate acid in accordance with customary methods.

Possible diluents for process variant (b), involving reaction of the compounds of the formula (IV) with 1,2,4-triazoles of the formula (III), include all inert high-boiling organic solvents. Preferred examples include aromatic hydrocarbons, such as chlorobenzene. The water of reaction produced can be removed azeotropically by means of this solvent. Process variant (b) can also be carried out without solvents, for example in the melt.

It may be appropriate, when carrying out process variant (b), to add a dehydrating agent, preferably an alkaline earth metal oxide, such as MgO, BaO, CaO or aluminum oxide, to facilitate the splitting off of water.

The reaction temperatures can be varied over a wide range in process variant (b). In general, the reaction is carried out at about 100° to 230° C., preferably about 140° to 200° C. and especially about 170° to 190° C. If a solvent is present, the reaction may be appropriately carried out at the boiling point of the particular solvent.

When carrying out process variant (b), it is preferred to use 1 to 2 moles of 1,2,4-triazole, and 1 to 3 moles of dehydrating agent when employed, for each mole of the compound of the formula (IV). The products of the formula (I) may be isolated in accordance with customary methods.

Possible diluents in the process variant (c) involving reaction of compounds of the formula (IV) with compounds of the formula (V), include all inert organic solvents. Preferred examples include aromatic hydrocarbons, such as benzene or toluene, ethers such as diethyl ether or tetrahydrofuran, chlorinated hydrocarbons, such as methylene chloride, chloroform or carbon tetrachloride, and lower alkyl nitriles, such as acetonitrile.

The reaction temperatures can be varied over a wide range in process variant (c). In general, the reaction is carried out at about 0° to 120° C., preferably about 20° to 100° C.

When carrying out the process variant (c), it is preferred to use about 1 mole of the compound of the formula (V) for each mole of the compound of the formula (IV). The products of the formula (I) may be isolated in accordance with customary methods.

As diluents in the process variant (d) involving reaction of compounds of the formula (VI) with 1,2,4-triazole hydrochlorides of the formula (VII), it is possible to use high-boiling polar organic solvents. Preferred examples include sulfoxides, such as dimethylsufoxide, formamides, such as dimethylformamide, and ethers, such as dioxane or dibutyl ether. The reaction according to process variant (d) is, however, preferably carried out without solvents, that is to say in the melt.

It can be appropriate to add an acid catalyst, for example hydrochloric acid or p-toluenesulfonic acid, when carrying out process variant (d), in order to facilitate the splitting off of alcohol or phenol.

The reaction temperatures can be varied over a wide range in process variant (d). In general, the reaction is carried out at about 80° to 250° C., preferably 120° to 200° C., especially 140° to 190° C. If a solvent is used, the process is appropriately carried out at the boiling point of the particular solvent.

In carrying out the process variant (d), it is preferred to use about 1 mole of 1,2,4-triazole hydrochloride, and 0.01 to 0.1 mole of acid catalyst if used, for each mole of the compound of the formula (VI).

To isolate the products of the formula (I), the reaction mixture may be taken up in water, whereupon it partly dissolves; the suspension may be neutralized with alkali or alkali carbonate and extracted with organic solvents which are slightly miscible with water, for example methylene chloride. The organic phase may be dried and the solvent distilled off. The resulting solid or oily residue may be purified by recrystallization.

The compounds of the formula (I) obtained according to the process variants (a), (b), (c) or (d) can be converted into functional derivatives of the keto grouping and/or into their salts in accordance with the customary methods.

The following are examples of the new active compounds of the invention which can be prepared in accordance with the process of the invention: [ω-(1,2,4-triazolyl-1')]-[ω-phenoxy]-acetophenone, [ω-(1,2,4-triazolyl-1')]-[ω-4'-chlorophenoxy]-acetophenone, [ω-(1,2,4-triazolyl-1')]-[ω-3'-chlorophenoxy]-acetophenone, [ω-(1,2,4-triazolyl-1')]-[ω-2',4'-dichlorophenoxy]-acetophenone, [ω-(1,2,4-triazolyl-1')]-[ω-2',4'-dichlorophenoxy]-4-chloroacetophenone, [ω-(1,2,4-triazolyl-1')]-[ω-2',6'-dichlorophenoxy]-acetophenone, [ω-(1,2,4-triazolyl-1')]-[ω-4'-methoxyphenoxy]-acetophenone, [ω-(1,2,4-triazolyl-1')]-[ω-4'-methylphenoxy]-acetophenone, [ω-(1,2,4-triazolyl-1')]-[ω-2'-methylphenoxy]-acetophenone, [ω-methyl]-[ω-(1,2,4-triazolyl-1')]-[ω-4'-chlorophenoxy]-acetophenone, [ω-phenyl]-[ω-(1,2,4-triazolyl-1')]-[ω-2',4'-dichlorophenoxy]-acetophenone, [ω-phenyl]-[ω-(1,2,4-triazolyl-1')]-[ω-2',5'-dichlorophenoxy]-acetophenone, [2-(1,2,4-triazolyl-1')]-[2-(2',4'-dichlorophenoxy)]-acetaldehyde, [1-(1,2,4-triazolyl-1')]-[1-(2',4'-dichlorophenoxy)]-propan-2-one, [2-(1,2,4-triazolyl-1')]-[2-phenoxy]-butan-3-one, [2-(1,2,4-triazolyl-1')]-[2-(4'-chlorophenoxy)]-butan-3-one, [2-(1,2,4-triazolyl-1')]-[2-(4'-fluorophenoxy]-butan-3-one, [2-(1,2,4-triazolyl-1')]-[2-(2',4'-dichlorophenoxy]-butan-3-one, [1-(1,2,4-triazolyl-1')]-[1-(2',4'-dichlorophenoxy)]-3-methyl-butan-2-one, [2-(1,2,4-triazolyl-1')]-[2-(4'-chlorophenoxy)]-4-methyl-pentan-3-one, [2-(1,2,4-triazolyl-1')]-[2-(2',4'-dichlorophenoxy)]-4-methyl-pentan-3-one, [1-(1,2,4-triazolyl-1')]-[1-(4'-chlorophenoxy)]-3,3-dimethyl-butan-2-one, [1-(1,2,4-triazolyl-1')]-[1-(2',4'-dichlorophenoxy)]-3,3-dimethyl-butan-2-one, [1-(1,2,4-triazolyl-1')]-[1-(2',5'-dichlorophenoxy)]-3,3-dimethyl-butan-2-one, [1-(1,2,4-triazolyl-1')]-[1-(2',6'-dichlorophenoxy)]-3,3-dimethyl-butan-2-one, [1-(1,2,4-triazolyl-1')]-[1-(2',4',6'-trichlorophenoxy)]-3,3-dimethyl-butan-2-one, [1-(1,2,4-triazolyl-1')]-[1-(2'-chlorophenoxy)]-3,3-dimethyl-butan-2-one, [1-(1,2,4-triazolyl-1')]-[1-(4'-bromophenoxy)]-3,3-dimethyl-butan-2-one, [1-(1,2,4-triazolyl-1')]-[1-(4'-fluorophenoxy)]-3,3-dimethyl-butan-2-one, [1-(1,2,4-triazolyl-1')]-[1-(4'-methylphenoxy)]-3,3-dimethyl-butan-2-one, [1-(1,2,4- triazolyl-1')]-[1-(4'-methoxyphenoxy)]-3,3-dimethyl-butan-2-one, [1-(1,2,4-triazolyl-1')]-[1-(4'-tert.-butylphenoxy)]-3,3-dimethyl-butan-2-one, [1-(1,2,4-triazolyl-1')]-[1-(4'-isopropylphenoxy)]-3,3-dimethyl-butan-2-one, [1-(1,2,4-triazolyl-1')]-[1-(2'-methyl-4'-chlorophenoxy)]-3,3-dimethyl-butan-2-one, [1-(1,2,4-triazolyl-1')]-[1-(4'-trifluoromethylphenoxy)]-3,3-dimethyl-butan-2-one, [1-(1,2,4-triazolyl-1')]-[1-(4'-nitrophenoxy)]-3,3-dimethyl-butan-2-one, [1-(1,2,4-triazolyl-1')]-[1-(2'-nitrophenoxy)]-3,3-dimethyl-butan-2-one, [1-(1,2,4-triazolyl-1')]-[1-(4'-fluorodichloromethylmercaptophenoxy)]-3,3-dimethyl-butan-2-one, [1-(1,2,4-triazolyl-1')]-[1-(4'-chloromethylsulphonyl-phenoxy)]-3,3-dimethyl-butan-2-one, [1-(1,2,4-triazolyl-1')]-[1-(p-diphenoxy)]-3,3-dimethyl-butan-2-one, [1-(1,2,4-triazolyl-1')]-[1-(o-diphenoxy)]-3,3-dimethyl-butan-2-one, [2-(1,2,4-triazolyl-1')]-[2-phenoxy]-4-dimethyl-pentan-3-one, [2-(1,2,4-triazolyl-1')]-[2-(4-fluorophenoxy)]-4-dimethyl-pentan-3-one, [2-(1,2,4-triazolyl-1')]-[2-(2',4'-dichlorophenoxy)]-4-dimethyl-pentan-3-one, [1-phenyl]-[1-(1,2,4-triazolyl-1')]-[1-phenoxy]-3,3-dimethyl-butan-2-one, [1-phenyl]-[1-(1,2,4-triazolyl-1')]-[1-(4'-fluorophenoxy)]-3,3-dimethyl-butan-2-one, [1-phenyl]-[1-(1,2,4-triazolyl-1')]-[1-(2',4'-dichlorophenoxy)]-3,3-dimethyl-butan-2-one, [2-(1,2,4-triazolyl-1')]-[2-(2',4'-dichlorophenoxy)]-1-cyclohexyl-ethan-1-one, [2-(1,2,4-triazolyl-1')]-[2-(2',4'-dichlorophenoxy)]-1-cyclopentyl-ethan-1-one, and [2-(1,2,4-triazolyl-1')]-[2-(2',4'-dichlorophenoxy)]-3-cyclohexyl-propan-3-one, as well as their salts, for example the hydrochlorides.

As particularly active compounds there may be mentioned: [1-(1,2,4-triazolyl-1')]-[1-(4'-chlorophenoxy)]-3,3-dimethylbutan-2-one and its hydrochloride, and [1-(1,2,4-triazolyl-1')]-[1-(2',4'-dichlorophenoxy)]-3,3-dimethyl-butan-2-one and its hydrochloride.

The active compounds according to the invention display a strong fungitoxic action. They do not appear to damage crop plants at the concentrations necessary for combating fungi and are of low toxicity to warm-blooded animals. For these reasons they are suitable for use as plant protection agents for combating fungi. Fungitoxic agents are employed in plant protection for combating Archimycetes, Phycomycetes, Ascomycetes, Basidiomycetes and Fungi Imperfecti.

The active compounds according to the invention have a very broad spectrum of action and can be used against parasitary fungi which infect above-ground parts of the plants or which attack plants through the soil, and against seed-borne pathogens.

They display a particularly good activity against parasitary fungi on above-ground parts of plants, such as species of Erysiphe and species of Venturia, and also against species of Piricularia and Pellicularia, for example against the pathogens responsible for powdery mildew of apple (*Podosphaera leucotricha*), apple scab (*Fusicladium dendriticum*) and bunt of wheat (*Tilletia tritici*). It is to be emphasized that the active compounds according to the invention not only display a protective action but also are active curatively, that is to say when used after contamination with the spores of the fungus. Furthermore, attention should be drawn to the systemic action of the substances. Thus it is possible to protect plants against fungal attack if the active compound is supplied to the above-ground parts of the plant via the soil and the root. As plant protection agents, the substances according to the invention can be used for soil treatment, for seed treatment and for the treatment of above-ground parts of plants.

The substances according to the invention show good toleration by plants. They possess only slight toxicity towards warm-blooded animals and because of their slight odor and their good toleration by human skin they are not unpleasant to handle.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides or insecticides, acaricides, rodenticides, bactericides, nematocides, herbicides, fertilizers, bird repellents, growth-enhancing compounds, growth-regulating agents, agents for improving soil structure, etc., if desired, or in the form of particular dosage preparations for specific application made therefrom, such as solutions, emulsions, suspensions, powders, pastes, and granules which are thus ready for use.

The formulations in general contain from 1 to 95 percent by weight of active compound, preferably 5 to 90 percent.

When used as leaf fungicides, the concentrations of active compound in the compositions applied can be varied over a wide range. They are generally from 0.1 to 0.00001 percent by weight, preferably 0.05 to 0.0001.

In the dressing of seed, amounts of active compound of 0.01 to 50 g per kilogram of seed, preferably 0.01 to 5 g, are in general required.

For soil treatment, amounts of active compound of 1 to 1,000 g per cubic meter of soil, preferably 10 to 200 g, are in general required.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Erysiphe test
Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23°–24° C. and at a relative atmospheric humidity of about 75%.

After 12 days, the infection of the cucumber plants was determined as a percentage of the untreated but also inoculated control plants. 0% means no infection; 100% that the infection was exactly as great as in the case of the control plants.

The active compounds, the concentrations of the active compounds and the results can be seen from the following Table 1.

Table 1

| | Erysiphe Test | | |
|---|---|---|---|
| | Infection in % of the infection of the untreated control at an active compound concentration of | | |
| Active compound | 0.00019% | 0.000125% | 0.00009% |
| 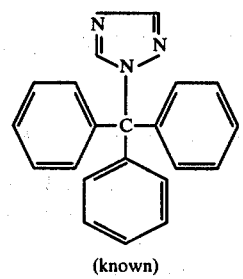 (known) | 83 | — | — |
| 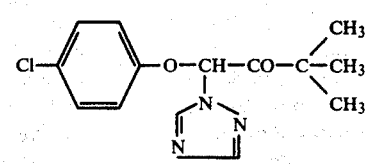 (A) (2) | 19 | | 25 |

Table 1-continued

Erysiphe Test

| Active compound | | Infection in % of the infection of the untreated control at an active compound concentration of | | |
|---|---|---|---|---|
| | | 0.00019% | 0.000125% | 0.00009% |
| Compound with 2,4-dichlorophenoxy, triazolyl, tert-butyl ketone structure | (1) | 16 | | 37 |
| Compound with 4-nitrophenoxy, triazolyl, tert-butyl ketone structure | (17) | | 50 | |
| Compound with 2,4-dichlorophenoxy, phenyl, triazolyl, tert-butyl ketone·HCl structure | (46′) | | 10 | |
| Compound with 4-tert-butylphenoxy, triazolyl, tert-butyl ketone structure | (4) | | 41 | |
| Compound with 4-chlorophenoxy, triazolyl, tert-butyl ketone·HCl structure | (2′) | | 21 | |
| Compound with 4-chlorophenoxy, phenyl, triazolyl, tert-butyl ketone structure | (5) | | 0 | |

EXAMPLE 2

Podosphaera test (powdery mildew of apples) [Protective]
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated by dusting with conidia of the apple powdery mildew causative organism (*Podosphaera leucotricha* Salm.) and placed in a greenhouse at a temperature of 21°–23° C. and at a relative atmospheric humidity of about 70%.

Ten days after the inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following Table 2

Table 2
Podosphaera Test/Protective
| Active Compound | | Infection in % of the infection of the untreated control at an active compound concentration of | | |
|---|---|---|---|---|
| | | 0.00078% | 0.00062% | 0.00039% |
| 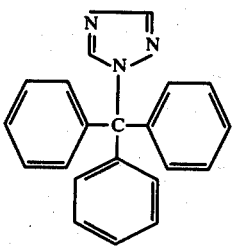 (known) | (A) | 52 | | 61 |
| 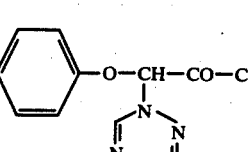 | (2) | 26 | | 39 |
| 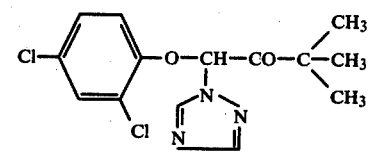 | (1) | 28 | | 26 |
| 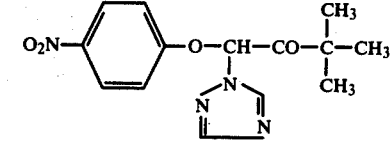 | (17) | 24 | | |
| 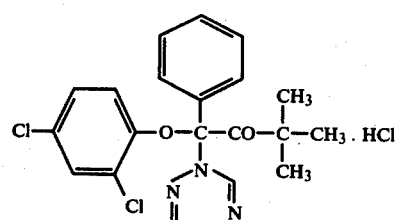 | (46') | 26 | | |
| 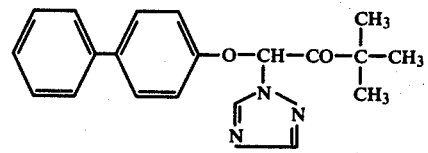 | (19) | 16 | | |
| 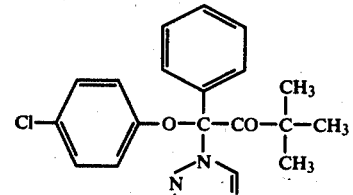 | (5) | 0 | | |
EXAMPLE 3
Fusicladium test (apple scab) (Protective)
Solvent: 4.7 parts by weight of acetone
Emulsifier: 0.3 part by weight of alkylaryl polyglycol ether
Water: 93 parts by weight The amount of active compound required for the desired concentration of the active compound in the spray liquid was mixed with the stated amount of solvent, and the concentrate was diluted with the stated amount of water which contained the stated additions.

Young apple seedlings in the 4-6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum* Fuckel) and incubated for 18 hours in a humidity chamber at 18°-20° C. and at a relative atmospheric humidity of 100%.

The plants then again went into a greenhouse for 14 days.

15 days after inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following Table 3:

Table 3

Fusicladium Test/Protective

| Active Compound | | Infection in % of the infection of the untreated control at an active compound concentration of | | |
|---|---|---|---|---|
| | | 0.025% | 0.0025% | 0.00156% |
| 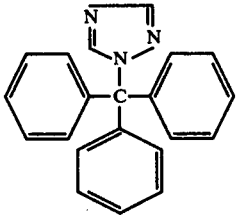 (known) | (A) | 97 | — | |
| 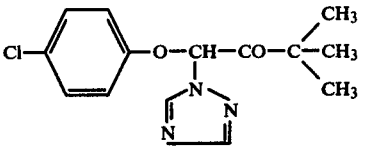 | (2) | 2 | | 26 |
| 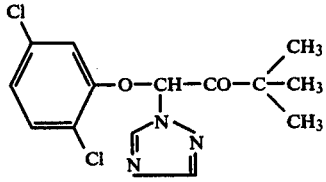 | (11) | 43 | | |
| 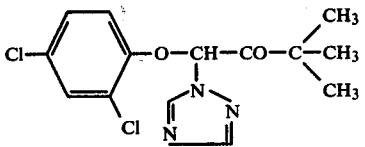 | (1) | 0 | | 11 |
| 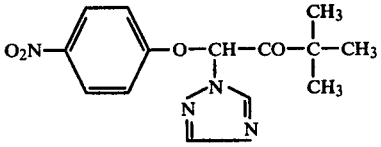 | (17) | 63 | | |
| 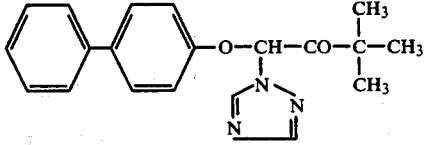 | (19) | 0 | | |

Table 3-continued

Fusicladium Test/Protective

| Active Compound | Infection in % of the infection of the untreated control at an active compound concentration of | | |
|---|---|---|---|
| | 0.025% | 0.0025% | 0.00156% |
| (20) phenyl-phenyl–O–CH(N-triazolyl)–CO–C(CH₃)₃ | | 61 | |
| (21) 4-Cl-C₆H₄–O–CH(N-triazolyl)–CO–C(CH₃)₃ · HCl | | 32 | |

EXAMPLE 4

Fusicladium test (apple scab) [Curative]
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were inoculated with an aqueous conidium suspension of the apple scab causative organism (*Fusicladium dendriticum* Fuckel) and incubated for 18 hours in a humidity chamber at 18°–20° C. and at an atmospheric humidity of 100%. The plants then went into a greenhouse where they dried.

After standing for a suitable period of time, the plants were sprayed dripping wet with the spray liquid prepared in the manner described above. The plants then again went into a greenhouse.

15 days after inoculation, the infection of the apple seedlings was determined as a percentage of the untreated but also inoculated control plants. 0% means no infection; 100% means that the infection was exactly as great as in the case of the control plants.

The active compounds, the concentrations of the active compounds, the period of time between inoculation and spraying and the results can be seen from the following Table 4:

Table 4

Fusicladium Test/Curative
42 Hour Dwell Time

| Active compound | | Infection in % of the infection of the untreated control at an active compound concentration of 0.025% |
|---|---|---|
| $C_{12}H_{25}NH-C(=NH)(NH_2) \cdot CH_3COOH$ (known) | (B) | 14 |
| 4-Cl-C₆H₄–O–CH(N-triazolyl)–CO–C(CH₃)₃ | (2) | 0 |
| 3,4-Cl₂-C₆H₃–O–CH(N-triazolyl)–CO–C(CH₃)₃ | (1) | 2 |
| biphenyl–O–CH(N-triazolyl)–CO–C(CH₃)₃ | (19) | 0 |
| 2,4-Cl₂-C₆H₃–O–CH(N-triazolyl)–CO–(4-Cl-C₆H₄) | (8) | 1 |

Table 4-continued
Fusicladium Test/Curative 42 Hour Dwell Time

| Active compound | | Infection in % of the infection of the untreated control at an active compound concentration of 0.025% |
|---|---|---|
| 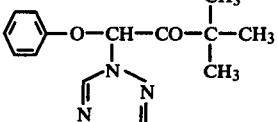 | (34) | 7 |

EXAMPLE 5

Erysiphe Test/Systemic
Solvent: 4.7 parts by weight of acetone
Dispersing Agent: 0.3 part by weight of alkylaryl polyglycol ether
Water: 95 parts by weight.

The amount of active compound required for the desired concentration of the active compound in the watering liquid was mixed with the stated amount of solvent and the concentrate was diluted with the stated amount of water, which contained the stated additions.

Cucumber plants grown in standard soil, in the 1–2 leaf stage, were watered three times over the course of one week with 20 ml of the watering liquid, at the stated active compound concentration, relative to 100 ml of soil.

After the treatment, the plants treated in this way were inoculated with conidia of the fungus *Erysiphe cichoracearum*. Thereafter the plants were placed in a greenhouse at 23°–24° C. and a relative atmospheric humidity of 70%. After 12 days, the infection of the cucumber plants in percent of the untreated but also inoculated control plants was determined.

0% denotes no infection and 100% denotes that the infection was exactly as high as in the case of the control plants.

The active compounds, active compound concentrations and results are shown in Table 5.

Table 5
Erysiphe Test/Systemic

| Active Compound | | Infection in % of the infection of the untreated control at an active compound concentration of | | |
|---|---|---|---|---|
| | | 30 ppm | 25 ppm | 15 ppm |
| 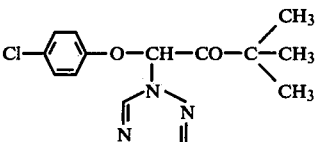 | (2) | | 0 | 0 |
| 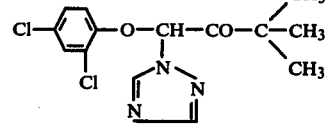 | (1) | | 0 | 0 |
| 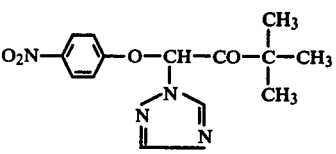 | (17) | | 0 | |
| 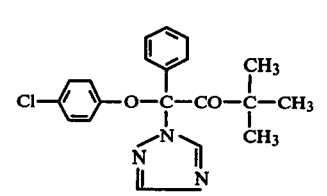 | (5) | | 0 | |

EXAMPLE 6

Fusicladium Test/Systemic
Solvent: 4.7 parts by weight of acetone
Emulsifier: 0.3 part by weight of alkylaryl polyglycol ether
Water: 95 parts by weight The amount of active compound required for the desired concentration of the active compound in the watering liquid was mixed with the stated amount of solvent and the concentrate was diluted with the stated amount of water which contained the stated addition.

Apple seedlings grown in standard soil, in the 3–4 leaf stage, were watered once over the course of a week with 20 ml of the watering liquid in the indicated concentration of active compound, relative to 100 ml of soil.

The plants treated in this way were inoculated, after the treatment, with an aqueous conidium suspension of *Fusicladium dentriticum* Fuckel and incubated for 18 hours in a humidity chamber at 18°–20° C. and at a relative atmospheric humidity of 100%. The plants then went into a greenhouse for 14 days.

15 days after inoculation, the infection of the seedlings was determined as a percentage of the untreated but also inoculated control plants. 0% means no infection; 100% means that the infection was exactly as great as in the case of the control plants.

The active compounds, the concentrations of the active compounds and the results can be seen from the following Table 6.

Table 6

Fusicladium Test/Systemic

| Active Compound | Infection in % of the infection of the untreated control at an active compound concentration of | |
|---|---|---|
| | 30 ppm | 25 ppm |
| 2,4-dichlorophenyl-O-CH(triazolyl)-CO-C(CH₃)₃ (1) | 4 | |
| 4-nitrophenyl-O-CH(triazolyl)-CO-C(CH₃)₃ (17) | 0 | |
| biphenyl-O-CH(triazolyl)-CO-C(CH₃)₃ (19) | 1 | |

Table 7

Pellicularia Test

| Active Compound | Infection in % of the infection of the untreated control at an active compound concentration of | |
|---|---|---|
| | 0.05% | 0.025% |
| triphenyl-triazolyl-methane (known) (A) | 100 | |
| 4-chlorophenyl-O-CH(triazolyl)-CO-C(CH₃)₃ (2) | 0 | 25 |
| 2,4-dichlorophenyl-O-CH(triazolyl)-CO-C(CH₃)₃ (1) | 0 | 50 |

EXAMPLE 7

Pellicularia Test
Solvent: 1.9 parts by weight of dimethylformamide
Dispersing Agent: 0.1 part by weight of alkylaryl polyglycol ether
Water 98 parts by weight The amount of active compound required for the desired concentration of the active compound in the spray liquid was mixed with the stated amount of the solvent and of the dispersing agent and the concentrate was diluted with the stated amount of water.

30 approximately 3 weeks old rice plants were sprayed with the spray liquid until dripping wet. The plants remained in a greenhouse at temperatures of 22° to 24° C. and a relative atmospheric humidity of about 70% until they had dried off. Thereafter the plants were infected with a culture of *Pellicularia sasakii* grown on malt agar and set up at 28 to 30° C. and 100% relative atmospheric humidity.

In the case of the plants infected with *Pellicularia sasakii* the infection was determined after 5–8 days on the leaf sheaths in relation to the untreated but infected control.

0% means no infection; 100% means that the infection was exactly as great as in the case of the control plants.

The active compounds, the concentrations of the active compounds and the results can be seen from the following Table 7.

EXAMPLE 8

(a) The starting material was prepared as follows:

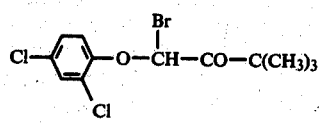

35.8 g (0.2 mole) of α-bromo-pinacolone in 50 ml of ethyl acetate were added dropwise to sodium 2,4-dichlorophenolate which was prepared from 32.6 g (0.2 mole) of 2,4-dichlorophenol and 4.6 g (0.2 mole) of sodium in 130 ml of absolute alcohol, and the mixture was heated to the boil over-night. Thereafter the sodium bromide produced was filtered off hot, the filtrate was distilled in vacuo and the solid residue was recrystallized from a little ligroin.

38 g (73% of theory) of 1-(2′,4′-dichlorophenoxy)-3,3-dimethyl-butan-2-one of melting point 65° C. were obtained.

(b) 6 ml (0.11 mole) of bromine were added to 26.1 g (0.1 mole) of 1-(2′,4′-dichlorophenoxy)-3,3-dimethyl-butan-2-one and the mixture was heated under reflux to 140° C. for 1 hour. The resulting oily residue was taken up with petroleum ether, whereupon it crystallized; the solid residue was filtered off and well rinsed.

30 g (89% of theory) of 1-bromo-1-(2′,4′-dichlorophenoxy)-3,3-dimethyl-butan-2-one of melting point 70° C. were obtained.

(c)

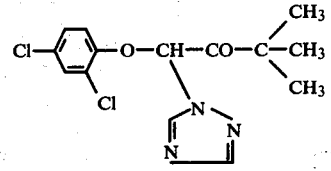

(1)

11.2 g (0.033 mole) of 1-bromo-1-(2',4'-dichlorophenoxy)-3,3-dimethyl-butan-2-one and 9.9 g (0.15 mole) of 1,2,4-triazole were dissolved in 80 ml of acetonitrile and heated under reflux for 48 hours. Thereafter the solvent was distilled off in vacuo, the residue was taken up with 150 ml of water and the aqueous solution was extracted by shaking three times with 40 ml of methylene chloride at a time. The organic phase was thereafter twice washed with 150 ml of water at a time, dried over sodium sulfate and distilled.

The oil obtained as a residue was fractionally recrystallized from a little ether, whereby first 1 g of a product of melting point 145° C., which was a by-product and was not identified, was obtained, followed by 7.6 g (70% of theory) of 1-[1,2,4-triazolyl-(1')]-1-[(2',4'-dichloro)-phenoxy]-3,3-dimethyl-butan-2-one of melting point 65° C.

(d) Preparation of the hydrochloride:

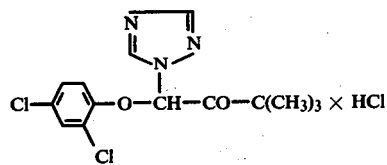

(1')

1-[1,2,4-triazolyl-(1')]-1-[(2',4'-dichloro)-phenoxy]-3,3-dimethyl-butan-2-one were suspended in anhydrous ether and treated with a solution of hydrochloric acid in ether. Thereupon the material gradually dissolved. The ether was distilled off in vacuo. The residue which remained was recrystallized from isopropanol.

The resulting [1-[1,2,4-triazolyl-(1')]-1-(2',4'-dichlorophenoxy)-3,3-dimethyl-butan-2-one] hydrochloride had a melting point of 153° C.

EXAMPLE 9

(a) The starting material was prepared as follows:

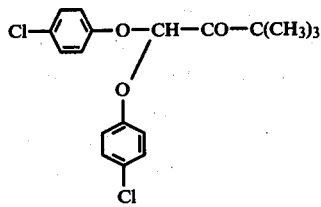

6.5 g (0.2 mole) of 80% strength sodium hydride were suspended in 100 ml of anhydrous acetonitrile and 27 g (0.21 mole) of 4-chlorophenol in 50 ml of acetonitrile were added dropwise at room temperature while stirring and cooling.

After completion of the evolution of hydrogen, a further 27 g (0.105 mole) of 1,1-dibromo-3,3-dimethyl-butan-2-produced one (manufactured according to Organic Synthesis 10, page 12) were added while stirring and cooling. Thereafter the mixture was slowly heated to the boil and boiled under reflux for 12 hours.

After cooling, the solvent was distilled off in vacuo, the residue was boiled up to hot ethyl, acetate, active charcoal was added, the whole was filtered and again briefly boiled up and the solution was distilled initially in vacuo, and in a high vacuum after the solvent had distilled over.

54 g. (76.5% of theory) of 1,1-bis-(4'-chloro-phenoxy)-3,3-dimethyl-butan-2-one of boiling point b.p.$_{0.1}$ 150° C. were obtained. The viscous oil solidified after some time.)

b)

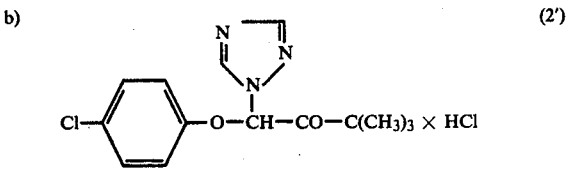

(2')

17.7 g (0.05 mole) of 1,1-bis-(4'-chlorophenoxy)-3,3-dimethyl-butan-2-one were intimately mixed with 5.9 g (0.055 mole) of 1,2,4-triazole hydrochloride and the mixture was heated to 220° C over the course of one hour and left at this temperature for 30 minutes; on doing so, the 4-chlorophenol split off commenced to boil.

After cooling, 100 ml of 10% strength sodium hydroxide solution, covered with 200 ml of ether, were added. The ether phase was separated off and washed three times with 30 ml of 5% strength sodium hydroxide solution at a time and twice with 50 ml of water at a time. After drying over sodium sulfate, the solvent was distilled off in vacuo. The oily residue was taken up in 100 ml of anhydrous ether and 0.055 mole of hydrogen chloride were passed into this solution. This a precipitate which after standing overnight was filtered off and rinsed with ether.

7.3 g (46% of theory) of 1-[1,2,4-triazolyl-(1')]-1-(4'-chlorophenoxy)-3,3-dimethyl-butan-2-one hydrochloride of melting point 103°-105° C. were obtained. — The melting point of the free base is 75° C. (compound (2)).

EXAMPLE 10

(a) ω-bromo-ω-(2',6'-dichloro)-phenoxy-acetophenone used as the starting material was prepared by condensation of 2,6-dichlorophenol with ω-chloroacetophenone and bromination of the resulting ω-(2',6'-dichloro)-phenoxy-acetophenone in the usual manner and had a melting point of 58° C.

(b)

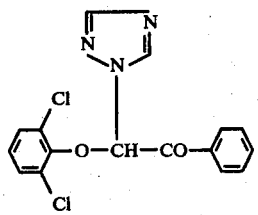

(3)

18.0 g (0.05 mole) of ω-bromo-ω-(2',6'-dichlorophenoxy)-acetophenone and 15 g (0.22 mole) of 1,2,4-triazole were dissolved in 120 ml of acetonitrile and the solution was heated under reflux for 48 hours. After distilling off the solvent in vacuo, the residue was taken up in 400 ml of water. This aqueous solution was extracted with methylene chloride as described and the organic phase was twice washed with 100 ml of water at a time and then dried over sodium sulfate, and the solvent was distilled off in vacuo. The oily residue obtained crystallized on heating with ether.

After recrystallization from ethylene chloride, 7 g (40% of theory) of ω-[1,2,4-triazolyl-(1')]-ω-[(2',6'-dichloro)-phenoxy]-acetophenone of melting point 166° C. were obtained.

EXAMPLE 11

(a) 1-bromo-1-[(4'-tert.-butyl)-phenoxy]-3,3-dimethyl-butan-2-one (melting point 50° C.) used as the starting material was obtained by condensation of p-tert.-butyl-phenol with α-bromopinacolone-(2) and subsequent bromination.

(b)

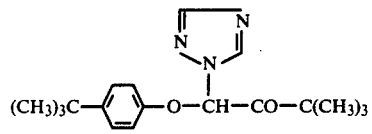

(4)

39 g (0.12 mole) of 1-bromo-1-(4'-tert.-butyl)-phenoxy-3,3-dimethyl-butan-2-one and 24 g (0.35 mole) of 1,2,4-triazole were dissolved in 240 ml of acetonitrile and heated to the boil under reflux for 24 hours. Thereafter the solvent was distilled off in vacuo and the residue was mixed with ice water and extracted three times with 40 ml of methylene chloride at a time. After removing the organic phase, the latter was washed twice with 200 ml of water at a time and dried over sodium sulfate, and the solvent was distilled off in vacuo.

The residue was recrystallized from ligroin. 26 g (69% of theory) of 1-[1,2,4-triazolyl-(1')]-1-[(4'-tert.-butyl)-phenoxy]-3,3-dimethyl-butan-2-one of melting point 115° C. were obtained.

EXAMPLE 12

(a) The starting material was prepared as follows:

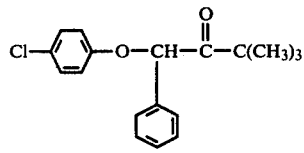

The Grignard compound was prepared from 38 g (0.3 mole) of benzyl chloride and 7.3 g (0.3 mole) of magnesium in 300 ml of anhydrous ether. 21 g (0.25 mole) of pivalonitrile in 100 ml of anhydrous ether were added dropwise at the boil and the mixture was kept boiling under reflux for 3 hours.

After cooling, the reaction mixture was added to 1.5 liters of ice water, the ether phase was separated off and discarded and the aqueous phase was stirred for 2 hours on a waterbath. In the course thereof, the mixture gradually assumed as oily consistency. The oil was repeatedly extracted with 250 ml of methylene chloride and the organic phase was washed with water, dried and subjected to vacuum distillation.

40.5 g (92% of theory) of 1-phenyl-3,3-dimethyl-butan-2-one of boiling point $b.p._{18}$ 86°–88° C. were obtained.

(b) 17.6 g (0.1 mol) of 1-phenyl-3,3-dimethyl-butan-2-one were dissolved in 100 ml of carbon tetrachloride, 5 ml (0.1 mole) of bromine were added dropwise thereto while stirring and under reflux, and the mixture was heated to the boil for one hour. After cooling, the distilling off the solvent, 25.4 g of 1-bromo-1-phenyl-3,3-dimethyl-butan-2-one of melting point 38°–42° C. were obtained in quantitative yield.

(c) A solution of 25.4 g (0.1 mole) of 1-bromo-1-phenyl-3,3-dimethyl-butan-2-one in 50 ml of ethyl acetate was added dropwise, at the boil, to a solution of 12.85 g (0.1 mole) of 4-chlorophenol and 2.3 g (0.1 mole) of sodium in 100 ml of ethanol. After boiling for 12 hours under reflux, the sodium bromide which had separated out was filtered off hot. The filtrate was distilled in vacuo and the solid residue which remained was recrystallized from ligroin. 20.2 g (67% of theory) of 1-phenyl-1-(4'-chlorophenoxy)-3,3-dimethyl-butan-2-one of melting point 103° C. were obtained.

(d)

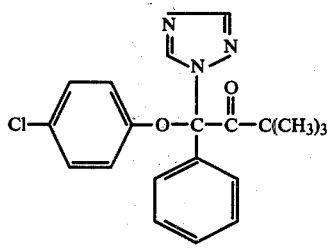

(5)

19.0 g (0.05 mole) of 1-bromo-1-phenyl-1-(4'-chlorophenoxy)-3,3-dimethyl-butan-2-one were dissolved in 120 ml of acetonitrile; thereafter 12 g (0.175 mole) of 1,2,4-triazole were added and the solution was heated for 12 hours under reflux. After distilling off the solvent in vacuo. 200 ml of ice water were added. The mixture was then extracted four times with 50 ml of methylene chloride at a time and the organic phase was removed and washed three times with 50 ml of water at a time. It was dried and the solvent was distilled off in vacuo. The oily residue was recrystallized from ligroin.

5.3 g (29% of theory) of 1-phenyl-1-(4'-chlorophenoxy)-1-[1,2,4-triazolyl-(1')]-3,3-dimethyl-butan-2-one of melting point 130° C. were obtained.

EXAMPLE 13

The compounds listed below were prepared analogously. These compounds were all of formula (I) in which $X^1$ and $X^2$ are hydrogen and Y is CO, while the meanings of $R^1$, $R^2$ and $R^3$ are given in the table.

| Compound | $R^1$ | $R^2$ | $R^3$ | Melting point, ° C. |
|---|---|---|---|---|
| 6 | ⟨phenyl⟩ | H | ⟨phenyl⟩ | 65–70 |

-continued

| Compound | R¹ | R² | R³ | Melting point, °C. |
|---|---|---|---|---|
| 7 | 2,4-dichlorophenyl | H | phenyl | |
| 8 | 2,4-dichlorophenyl | H | 4-chlorophenyl | 101–104 |
| 9 | 2-chlorophenyl | H | $C(CH_3)_3$ | 110 |
| 10 | 2,3-dichlorophenyl | H | $C(CH_3)_3$ | 186 |
| 11 | 2,5-dichlorophenyl | H | $C(CH_3)_3$ | 110 |
| 12 | 4-bromophenyl | H | $C(CH_3)_3$ | 89–92 |
| 13 | 4-fluorophenyl | H | $C(CH_3)_3$ | boiling point 0.3 at 160° C. |
| 14 | 4-methylphenyl | H | $C(CH_3)_3$ | 80 |
| 15 | 4-isopropylphenyl | H | $C(CH_3)_3$ | 76 |
| 16 | 4-chloro-2-methylphenyl | H | $C(CH_3)_3$ | 94–96 |
| 17 | 4-nitrophenyl | H | $C(CH_3)_3$ | 129 |

-continued

| Compound | R¹ | R² | R³ | Melting point, °C. |
|---|---|---|---|---|
| 18 | 4-(F₃C)C₆H₄– | H | C(CH₃)₃ | 106 |
| 19 | 4-biphenylyl | H | C(CH₃)₃ | 105–106 |
| 20 | 2-biphenylyl | H | C(CH₃)₃ | 70–73 |
| 21 | 4-(H₂N)C₆H₄– | H | C(CH₃)₃ | 122–125° C. |
| 22 | C₆H₅– | CH₃ | C(CH₃)₃ | |
| 23 | 4-ClC₆H₄– | CH₃ | C(CH₃)₃ | |
| 24 | 2,4-Cl₂C₆H₃– | H | CH₃ | hydrochloride 125–131 |
| 25 | 2,4-Cl₂C₆H₃– | CH₃ | CH₃ | |
| 26 | 4-ClC₆H₄– | CH₃ | CH₃ | |
| 27 | C₆H₅– | CH₃ | CH₃ | |
| 28 | 2,4-Cl₂C₆H₃– | H | CH(CH₃)₂ | 115 |

-continued

| Compound | R¹ | R² | R³ | Melting point, °C. |
|---|---|---|---|---|
| 29 | 2,4-diCl-C₆H₃– | CH₃ | CH(CH₃)₂ | |
| 30 | 4-Cl-C₆H₄– | CH₃ | CH(CH₃)₂ | |
| 31 | 2,4-diCl-C₆H₃– | H | cyclohexyl | 98 |
| 32 | 2,4-diCl-C₆H₃– | H | cyclopentyl | 102 |
| 33 | 2,4-diCl-C₆H₃– | C₆H₅ | C₆H₅ | |
| 34 | C₆H₅– | H | C(CH₃)₃ | 62 |
| 35 | 2,3-di(CH₃)-C₆H₃– | H | C(CH₃)₃ | boiling point$_{0.1}$/ 151° C (f.p. 76) |
| 36 | 2,4-di(CH₃)-C₆H₃– | H | C(CH₃)₃ | boiling point$_{0.1}$/ 145° C (f.p. 71) |
| 37' | C₆H₅– | C₆H₅– | C(CH₃)₃ | hydrochloride 138 |
| 38' | 4-Cl-C₆H₄– | H | CH₃ | hydrochloride 78–81 |
| 39' | 2,3-diCl-C₆H₃– | H | C₆H₅– | hydrochloride 126 |

-continued

| Compound | R¹ | R² | R³ | Melting point, °C |
|---|---|---|---|---|
| 40 | 2,4,5-trichlorophenyl | H | $C(CH_3)_3$ | 142–145 |
| 41 | 4-chloro-2-methylphenyl | H | $C(CH_3)_3$ | 114 |
| 42 | 3-chloro-4-methylphenyl | H | $C(CH_3)_3$ | 88–89 |
| 43 | 3-chloro-2,4-dimethylphenyl (CH₃, Cl, CH₃ substituted) | H | $C(CH_3)_3$ | 101 |
| 44 | dichloro-(trifluoromethyl)phenyl (Cl₂, CF₃) | H | $C(CH_3)_3$ | 135–138 |
| 45 | 3-(trifluoromethyl)phenyl | H | $C(CH_3)_3$ | 74–75 |
| 46' | 2,4-dichlorophenyl | phenyl | $C(CH_3)_3$ | hydrochloride 133–138 |
| 47 | 3-chlorophenyl | H | $C(CH_3)_3$ | 65–67 |
| 48 | 4-bromo-3-chlorophenyl | H | $C(CH_3)_3$ | 94–96 |

-continued

| Compound | R¹ | R² | R³ | Melting point, °C. |
|---|---|---|---|---|
| 49 | 2-methoxyphenyl | H | C(CH₃)₃ | 87 |
| 50 | 2,5-dimethylphenyl | H | C(CH₃)₃ | 74 |
| 51 | 2-bromo-4-biphenylyl | H | C(CH₃)₃ | 125 |
| 52 | 3,4-dichlorophenyl | H | C(CH₃)₃ | 82–84 |
| 53 | 4-nitro-2-methylphenyl | H | C(CH₃)₃ | 154 |
| 54 | 3-chloro-4-nitrophenyl | H | C(CH₃)₃ | 100–104 |
| 2″ | 4-chlorophenyl | H | C(CH₃)₃ | Sulfate 141 |
| 2‴ | 4-chlorophenyl | H | C(CH₃)₃ | Nitrate 140 decomposition |
| 2^iv | 4-chlorophenyl | H | C(CH₃)₃ | 1,5-Naphthalene disulfonate 270–273 decomposition |
| 1″ | 2,4-dichlorophenyl | H | C(CH₃)₃ | Nitrate 129–133 |
| 1‴ | 2,4-dichlorophenyl | H | C(CH₃)₃ | Sulfate 145–148 |

-continued

| Compound | R¹ | R² | R³ | Melting point, °C. |
|---|---|---|---|---|
| 1^iv | 2,4-dichlorophenyl | H | C(CH₃)₃ | 1,5-Naphthalene-disulfonate 250 decomposition |
| 17' | 4-nitrophenyl | H | C(CH₃)₃ | Hydrochloride 126–130 |
| 17'' | 4-nitrophenyl | H | C(CH₃)₃ | Sulfate 169–170 |
| 17''' | 4-nitrophenyl | H | C(CH₃)₃ | Nitrate 140–141 |
| 17^iv | 4-nitrophenyl | H | C(CH₃)₃ | 1,5-Naphthalene disulfonate 255 decomposition |
| 55' | 2,4,6-trichlorophenyl | H | C(CH₃)₃ | Hydrochloride 150–60 |
| 56 | 4-iodophenyl | H | C(CH₃)₃ | 107–108 |
| 57' | 2-methylphenyl | H | C(CH₃)₃ | Hydrochloride 142–150 |
| 58 | 3-methylphenyl | H | C(CH₃)₃ | 70–72 |
| 59 | 2-fluorophenyl | H | C(CH₃)₃ | 73–74 |
| 60 | 3-bromophenyl | H | C(CH₃)₃ | 79–80 |

-continued

| Compound | R¹ | R² | R³ | Melting point, °C. |
|---|---|---|---|---|
| 61 | 2-nitrophenyl (methyl-NO₂ substituted phenyl) | H | C(CH₃)₃ | 90–93 |
| 62 | 4-biphenylyl | H | phenyl | 110–112 |
| 63 | 3-chloro-4-biphenylyl | H | C(CH₃)₃ | 107 |
| 64 | 3,5-dichloro-4-biphenylyl | H | C(CH₃)₃ | 145–150 |
| 19' | 4-biphenylyl | H | C(CH₃)₃ | 3H₃PO₄ 124–126 |
| 19'' | 4-biphenylyl | H | C(CH₃)₃ | citric acid (COOH-CH₂-C(OH)(COOH)-CH₂-COOH) 101–105 |
| 19''' | 4-biphenylyl | H | C(CH₃)₃ | CH₃-CH=CH-CH=CH-COOH 99–102 |
| 19^iv | 4-biphenylyl | H | C(CH₃)₃ | CH₃—SO₃—H oil |
| 19^v | 4-biphenylyl | H | C(CH₃)₃ | hydrochloride 143–146 |
| 19^vi | 4-biphenylyl | H | C(CH₃)₃ | sulfate 128–130 |
| 19^vii | 4-biphenylyl | H | C(CH₃)₃ | nitrate 130–131 |

EXAMPLE 14

Other compounds of formula (I) in which $X^1$ and $X^2$ are hydrogen and which were prepared analogously from analogous starting materials include the following:

| Compound | $R^1$ | $R^2$ | $R^3$ | Y | Melting point, °C |
|---|---|---|---|---|---|
| 65 | O₂N—⟨⟩— | H | C(CH₃)₃ | C=NOH | 187 |
| 66 | Cl—⟨⟩— | H | C(CH₃)₃ | C=NOH | 194–205 |
| 67 | (Cl₅-phenyl) | H | C(CH₃)₃ | C(OH)₂ | 206 |
| 68 | (2,4-Cl₂-phenyl) | H | C(CH₃)₃ | C=NOH | 204 |

EXAMPLE 15

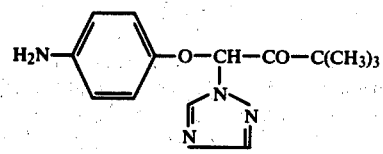
(21)

30.4 g (0.1 mole) of 1-[4′-nitrophenoxy]-1-[1,2,4-triazolyl-(1)]-3,3-dimethyl-butan-2-one are suspended in 300 ml of absolute ethanol. 13 g (0.25 mole) of hydrazine hydrate are added thereto and the mixture heated to 45° C. inside temperature. A suspension of 1.5 g of Raney nickel in 10 ml of absolute ethanol is slowly added to this reaction mixture (depending on the evolution of gas). After the nitro compound has completely dissolved, a little nickel is added and the mixture is heated for 1 hour under reflux. The product is thereafter filtered with suction in the hot state, washed with ethanol and the catalyst destroyed with 2N HCl. The solvent is removed from the filtrate by distillation in vacuo. The residual oil is thoroughly boiled with diisopropyl ether and filtered off by suction in the hot state. After drying of the residue there are obtained 5.7 g (21% of theory) of 1-[4′-aminophenoxy]-1-[1,2,4-triazolyl(1)]-3,3-dimethyl-butan-2-one with a melting point of 122°–125° C.

EXAMPLE 16

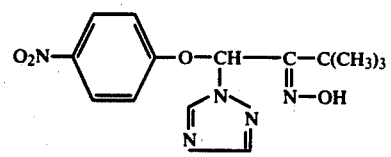
(65)

To 15.2 g (0.05 mole) of 1-[4′-nitrophenoxy]-1-[1,2,4-triazolyl(1)]-3,3-dimethyl-butan-2-one, dissolved in 250 ml ethanol and 100 ml of dioxane, there are initially added 4.1 g (0.05 mole) of anhydrous sodium acetate (→ yellow color) and then 3.5 g (0.05 mole) of hydroxyl ammonium chloride (→ decolorization). Stirring is carried out overnight at room temperature. 3.05 g (0.05 mole) of glacial acetic acid are added to this reaction mixture and heated for 12 hours under reflux. The mixture is then concentrated in vacuo to half its volume and poured onto 500 ml of water. After a short while crystals form. The solids are filtered off by suction and recrystallized from ethanol. 3.8 g (24% of theory) of 1-[4′-nitrophenoxy]-1-[1,2,4-triazolyl-(1)]-3,3-dimethyl-butan-2-oxime are obtained with a melting point of 187° C. (decomposition).

EXAMPLE 17

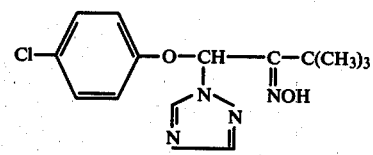
(66)

To 29.3 g (0.1 mole) of 1-[4′-chlorophenoxy]-1-[1,2,4-triazolyl(1)]-3,3-dimethyl-butan-2-one, dissolved in 150 ml of ethanol, there are first added 7 g (0.1 mole) of hydroxyl ammonium chloride and then 8.2 g (0.1 mole) of anhydrous sodium acetate. 6.6 g (0.11 mole) of glacial acetic acid are added and the reaction mixture then stirred overnight at room temperature. Thereafter concentration in vacuum is carried out until crystallization takes places. The product is then taken up in the hot state in approximately 200 ml of glacial acetic acid and filtered off at boiling point from undissolved substances. The filtrate is cooled whereupon crystallization occurs. There are obtained 10.7 g (35% of theory) of 1-[4′-chlorophenoxy]-1-[1,2,4-triazolyl-(1)]-3,3-dimethyl-butan-2-oxime with a melting point of 194°–205° C.

It will be appreciated that the instant specification and examples are set forth by way of illustration and not limitation, and that various modifications and changes may be made without departing from the spirit and scope of the present invention.

EXAMPLE 18

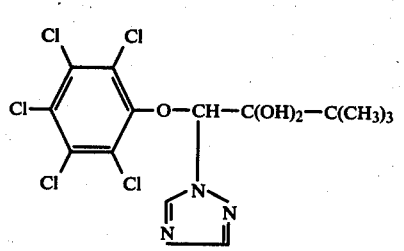
(67)

44 g (0.1 mole) of 1-bromo-1-pentachlorophenoxy-3,3-dimethyl-butan-2-one and 24 g (0.35 mole) of 1,2,4-triazole were heated under reflux for 15 hours. After distilling off the solvent in vacuo, the residue was taken up and stirred in water. After filtering off and drying the residue was recrystallized from acetic ester. 13.5 g (27% of theory) of 1-[1,2,4-triazolyl-(1′)]-1-(pentachlorophenoxy)-3,3-dimethyl-butan-2-one of melting point 206°–207° C. were obtained.

The starting product was obtained by bromination of the corresponding ether in carbon tetrachloride in the presence of a small amount of phosphorus tribromide. The product of melting point 103°–105° C. was obtained in a yield of 80% of theory.

What is claimed is:

1. A fungicidal composition comprising a fungicidally effective amount of a 1-substituted-1,2,4-triazole of the formula

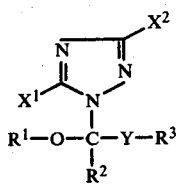

in which
X$^1$ and X$^2$ each independently is hydrogen or alkyl of 1 to 3 carbon atoms,
R$^1$ is alkyl of 1 to 8 carbon atoms, alkenyl of 2 to 6 carbon atoms, alkynyl of 2 to 6 carbon atoms, cycloalkyl of 5 to 7 carbon atoms, cycloalkenyl of 5 to 7 carbon atoms, or optionally substituted aryl of 6 to 10 carbon atoms or optionally substituted aralkyl of 6 to 10 carbon atoms in the aryl moiety and 1 to 2 carbon atoms in the alkyl moiety, the optional substituents being selected from the group consisting of halogen, nitro, amino, alkyl of 1 to 6 carbon atoms, alkoxy of 1 to 4 carbon atoms, alkylthio of 1 to 4 carbon atoms, haloalkyl of 1 to 2 carbon atoms and 1 to 5 halogen atoms, haloalkylthio of 1 to 2 carbon atoms and 3 to 5 halogen atoms, haloalkylsulfonyl of 1 to 2 carbon atoms and 1 halogen atom and o- or p-linked phenyl,
R$_2$ and R$^3$ each independently is hydrogen, alkyl of 1 to 8 carbon atoms, alkenyl of 2 to 6 carbon atoms, alkynyl of 2 to 6 carbon atoms, cycloalkyl of 5 to 7 carbon atoms, cycloalkenyl of 5 to 7 carbon atoms, or optionally substituted aryl of 6 to 10 carbon atoms or optionally substituted aralkyl of 6 to 10 carbon atoms in the aryl moiety and 1 to 2 carbon atoms in the alkyl moiety, the optional substituents being selected from the group consisting of halogen, nitro, alkyl of 1 to 4 carbon atoms, or haloalkyl of 1 or 2 carbon atoms and 1 to 5 halogen atoms, and
Y is —C(O)—, —C(OH)$_2$— or —C(OR)$_2$— wherein R is methyl or ethyl,
or a salt thereof, in admixture with a liquid hydrocarbon or chlorinated hydrocarbon diluent selected from the group consisting of aromatic hydrocarbons, halogenated aromatic hydrocarbons, cycloalkanes, and chlorinated aliphatic hydrocarbons.

2. The method of combating fungi that infect or attack plants which comprises applying to plants, seed or soil a fungicidally effective amount of a 1,2,4-triazole derivative of the formula

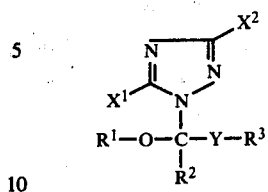

in which
X$^1$ and X$^2$ each independently is hydrogen or alkyl of 1 to 3 carbon atoms,
R$^1$ is alkyl of 1 to 8 carbon atoms, alkenyl of 2 to 6 carbon atoms, alkynyl of 2 to 6 carbon atoms, cycloalkyl of 5 to 7 carbon atoms, cycloalkenyl of 5 to 7 carbon atoms, or optionally substituted aryl of 6 to 10 carbon atoms or optionally substituted aralkyl of 6 to 10 carbon atoms in the aryl moiety and 1 to 2 carbon atoms in the alkyl moiety, the optional substituents being selected from the group consisting of halogen, nitro, amino, alkyl of 1 to 6 carbon atoms, alkoxy of 1 to 4 carbon atoms, alkylthio of 1 to 4 carbon atoms, haloalkyl of 1 to 2 carbon atoms and 1 to 5 halogen atoms, haloalkylthio of 1 to 2 carbon atoms and 3 to 5 halogen atoms, haloalkylsulfonyl of 1 to 2 carbon atoms and 1 halogen atom and o- or p-linked phenyl,
R$_2$ and R$^3$ each independently is hydrogen, alkyl of 1 to 8 carbon atoms, alkenyl of 2 to 6 carbon atoms, alkynyl of 2 to 6 carbon atoms, cycloalkyl of 5 to 7 carbon atoms, cycloalkenyl of 5 to 7 carbon atoms, or optionally substituted aryl of 6 to 10 carbon atoms or optionally substituted aralkyl of 6 to 10 carbon atoms in the aryl moiety and 1 to 2 carbon atoms in the alkyl moiety, the optional substituents being selected from the group consisting of halogen, alkyl of 1 to 6 carbon atoms, or haloalkyl of 1 or 2 carbon atoms and 1 to 5 halogen atoms, and
Y is —C(O)—, —C(OH)$_2$— or —C(OR)$_2$— wherein R is methyl or ethyl,
or a salt thereof.

3. The method according to claim 2 in which said compound is:
1-[1,2,4-triazolyl-(1')]-1-[(2',4'-dichloro)-phenoxy]-3,3-dimethyl-butan-2-one,
1-phenyl-1-(4'-chloro-phenoxy)-1-[1,2,4-triazolyl-(1')]-3,3-dimethyl-butan-2-one,
1-[1,2,4-triazolyl-(1')]-1-[(4'-nitro)-phenoxy]-3,3-dimethyl-butan-2-one, or
1-[1,2,4-triazolyl-(1')]-1-[(4'-chloro)-phenoxy]-3,3-dimethyl- butan-2-one.

* * * * *